(12) United States Patent
Langer et al.

(10) Patent No.: US 6,388,043 B1
(45) Date of Patent: May 14, 2002

(54) SHAPE MEMORY POLYMERS

(75) Inventors: Robert S. Langer, Newton, MA (US); Andreas Lendlein, Aachen (DE)

(73) Assignee: MnemoScience GmbH, Aachen (DE)

( * ) Notice: Subject to any disclaimer, the term of this patent is extended or adjusted under 35 U.S.C. 154(b) by 0 days.

(21) Appl. No.: 09/256,626

(22) Filed: Feb. 23, 1999

Related U.S. Application Data

(60) Provisional application No. 60/075,569, filed on Feb. 23, 1998.

(51) Int. Cl.$^7$ .............................................. C08G 18/48

(52) U.S. Cl. ........................... 528/80; 528/76; 528/176; 528/272; 528/193; 528/196; 528/271; 525/415; 525/440; 525/450; 525/903

(58) Field of Search ...................... 528/80, 76; 525/415, 525/440, 450, 903

(56) References Cited

U.S. PATENT DOCUMENTS

| | | |
|---|---|---|
| 4,575,373 A | 3/1986 | Johnson |
| 4,596,728 A | 6/1986 | Yang et al. |
| 4,804,733 A | 2/1989 | Bataille |
| 4,816,094 A | 3/1989 | Pomplun et al. |
| 5,049,591 A | 9/1991 | Hayashi et al. |
| 5,108,755 A | 4/1992 | Daniels |
| 5,128,197 A | 7/1992 | Kobayashi et al. |
| 5,139,832 A | 8/1992 | Hayashi et al. |
| 5,145,935 A | 9/1992 | Hayashi |
| 5,189,110 A | 2/1993 | Ikematu et al. |
| 5,418,261 A | 5/1995 | Helsemans et al. |
| 5,506,300 A | 4/1996 | Ward et al. |
| 5,591,786 A | 1/1997 | Oxman et al. |
| 5,635,545 A | 6/1997 | Oxman et al. |
| 5,665,822 A | 9/1997 | Bitler et al. |
| 5,665,831 A | 9/1997 | Neuenschwander et al. |
| 5,765,682 A | 6/1998 | Bley et al. |
| 5,776,162 A | 7/1998 | Kleshinski |
| 5,800,516 A | 9/1998 | Fine et al. |

FOREIGN PATENT DOCUMENTS

| | | |
|---|---|---|
| DE | 42 26 465 A1 | 2/1993 |
| EP | 0 374 961 A2 | 6/1990 |
| EP | 0 385 443 A2 | 9/1990 |
| EP | 0 422 693 A2 | 4/1991 |
| JP | 03068611 | 3/1991 |
| WO | WO 95/34331 A1 | 12/1995 |
| WO | WO 98/14803 A1 | 4/1998 |

OTHER PUBLICATIONS

Cederstrom & Van Humbeeck, "Relationship between shape memory material properties and applications," *Journal de Physique IV* 5:C2–335–41 (1995).

Dagani, "Intelligent Gels," *Chemistry & Engineering News* 75:29–37 (1997).

Echigo, et al., "Development of a new transvenous patent ductus arteriosus occlusion technique using a shape memory polymer," *ASAIO Trans.* 36(3):M195–8 (1990).

Gordon, "Applications of Shape Memory Polyurethanes," Proceedings of the First International Conference on Shape Memory and Superelastic Technologies, SMST International Committee, pp. 115–119 (1994).

Hayashi, et al., "Properties and applications of polyurethane–series shape memory polymer," *ANTEC* 1998–2001 (1994).

He, et al., "Higher order structure and thermo–responsive properties of polymeric gel with crystalline side chains," *Polymer Journal* 28:452–7 (1996).

Ito, et al., "Variation of free volume size and content of shape memory polymer–polyurethane–upon temperature studied by positron annihilation lifetime techniques and infrared spectroscopy," *J. Radioanalytical and Nuc. Chem.* 211:53–60 (1996).

Kagami, et al., "Shape memory behaviors of crosslinked copolymers containing strearyl acrylate," *Macromol. Rapid Commun.* 17:539–543 (1996).

Kim, et al., "Polyurethanes having shape memory effect," *Polymer* 37(26):5781–93 (1996).

Li, et al., "Crystallinity and morphology of segmented polyurethanes with different soft–segment length," *J. Applied Polymer* 62:631–38 (1996).

Hu, et al., "Synthesis and application of modulated polymer gels," *Science* 269:525–527 (1995).

Li, et al., "Shape memory gels made by the modulated gel technology," *J. Appl. Polym. Sci.* 63:1173–78 (1997).

Linge & Dahm, "Praktische aspekte der verwendung von superelastischen drahtbogen in der edgewisetechnik," *Forschr. Kieferorthop.* 55:324–329 (1994).

(List continued on next page.)

*Primary Examiner*—Rachel Gorr
(74) *Attorney, Agent, or Firm*—Holland & Knight LLP

(57) ABSTRACT

Shape memory polymer compositions, articles of manufacture thereof, and methods of preparation and use thereof are described. The shape memory polymer compositions can hold more than one shape in memory. Suitable compositions include at least one hard segment and at least one soft segment. The $T_{trans}$ of the hard segment is preferably between −30 and 270° C. At least one of the hard or soft segments can contain a crosslinkable group, and the segments can be linked by formation of an interpenetrating network or a semi–interpenetrating network, or by physical interactions of the blocks. Objects can be formed into a given shape at a temperature above the $T_{trans}$ of the hard segment, and cooled to a temperature below the $T_{trans}$ of the soft segment. If the object is subsequently formed into a second shape, the object can return to its original shape by heating the object above the $T_{trans}$ of the soft segment and below the $T_{trans}$ of the hard segment. The compositions can also include two soft segments which are linked via functional groups which are cleaved in response to application of light, electric field, magnetic field or ultrasound. The cleavage of these groups causes the object to return to its original shape.

44 Claims, 5 Drawing Sheets

OTHER PUBLICATIONS

Nakasima, et al., "Potential application of shape memory plastic as elastic material in clinical orthodontics," *Eur. J. of Ortho.* 13:179–186 (1991).

Sakurai, et al., "Crystal transformation of styrene–butadiene block copolymer," *Polymer* 35:4288–9 (1992).

Takahashi, et al., "Structure and properties of shape–memory polyurethane block copolymers," *J. Applied Polymer Science* 60:1061–69 (1996).

Tobushi, et al., "Mechanical properties of shape memory polymer of polyurethane series," *JSME International Journal Series I* 35:296–302 (1992).

Tobushi, et al., "Thermomechanical properties in a thin film of shape memory polymer of polyurethane series," *SPIE* 2716:46–57 (1996).

White & Ward, "Softenable, shape–memory thermoplastic for use in biomedical devices," *Mat. Res. Soc. Symp. Proc.* 110:635–640 (1989).

P = THERMOPLASTIC MATERIALS

SOFT SEGMENT

HARD SEGMENT

O - JUNCTION UNIT

P0 - SEMICRYSTALLINE HOMOPOLYMERS, SEMICRYSTALLINE COPOLYMERS AND BLENDS THEREOF

P1 - THERMOPLASTIC ELASTOMERS WITH LINEAR CHAINS

P2 - THERMOPLASTIC ELASTOMERS WITH SIDE CHAINS OR ANY KIND OF DENDRITIC STRUCTURAL ELEMENTS

SHAPE MEMORY POLYMERS

CROSS-REFERENCE TO RELATED APPLICATIONS

Priority is claimed to U.S. Provisional application Serial No. 60/075,569, filed Feb. 23, 1998.

BACKGROUND OF THE INVENTION

This application is generally in the area of shape memory polymers, and more particularly to shape memory polymers having enhanced performance characteristics and more than one shape in memory.

Shape memory is the ability of a material to remember its original shape, either after mechanical deformation (FIG. 1), which is a one-way effect, or by cooling and heating (FIG. 2), which is a two-way effect. This phenomenon is based on a structural phase transformation.

The first materials known to have these properties were shape memory metal alloys (SMAs), including TiNi (Nitinol), CuZnAl, and FeNiAl alloys. The structure phase transformation of these materials is known as a martensitic transformation. These materials have been proposed for various uses, including vascular stents, medical guidewires, orthodontic wires, vibration dampers, pipe couplings, electrical connectors, thermostats, actuators, eyeglass frames, and brassiere underwires. These materials have not yet been widely used, in part because they are relatively expensive.

Scientists are actively developing shape memory polymers (SMPs) to replace or augment the use of SMAs, in part because the polymers are light, high in shape recovery ability, easy to manipulate, and economical as compared with SMAs. In the literature, SMPs are generally characterized as phase segregated linear block co-polymers having a hard segment and a soft segment. The hard segment is typically crystalline, with a defined melting point, and the soft segment is typically amorphous, with a defined glass transition temperature. In some embodiments, however, the hard segment is amorphous and has a glass transition temperature rather than a melting point. In other embodiments, the soft segment is crystalline and has a melting point rather than a glass transition temperature. The melting point or glass transition temperature of the soft segment is substantially less than the melting point or glass transition temperature of the hard segment.

When the SMP is heated above the melting point or glass transition temperature of the hard segment, the material can be shaped. This (original) shape can be memorized by cooling the SMP below the melting point or glass transition temperature of the hard segment. When the shaped SMP is cooled below the melting point or glass transition temperature of the soft segment while the shape is deformed, that (temporary) shape is fixed. The original shape is recovered by heating the material above the melting point or glass transition temperature of the soft segment but below the melting point or glass transition temperature of the hard segment. In another method for setting a temporary shape, the material is deformed at a temperature lower than the melting point or glass transition temperature of the soft segment, resulting in stress and strain being absorbed by the soft segment. When the material is heated above the melting point or glass transition temperature of the soft segment, but below the melting point (or glass transition temperature) of the hard segment, the stresses and strains are relieved and the material returns to its original shape. The recovery of the original shape, which is induced by an increase in temperature, is called the thermal shape memory effect.

Properties that describe the shape memory capabilities of a material are the shape recovery of the original shape and the shape fixity of the temporary shape.

Several physical properties of SMPs other than the ability to memorize shape are significantly altered in response to external changes in temperature and stress, particularly at the melting point or glass transition temperature of the soft segment. These properties include the elastic modulus, hardness, flexibility, vapor permeability, damping, index of refraction, and dielectric constant. The elastic modulus (the ratio of the stress in a body to the corresponding strain) of an SMP can change by a factor of up to 200 when heated above the melting point or glass transition temperature of the soft segment. Also, the hardness of the material changes dramatically when the soft segment is at or above its melting point or glass transition temperature. When the material is heated to a temperature above the melting point or glass transition temperature of the soft segment, the damping ability can be up to five times higher than a conventional rubber product. The material can readily recover to its original molded shape following numerous thermal cycles, and can be heated above the melting point of the hard segment and reshaped and cooled to fix a new original shape.

The shape memory effect exists for polymers (e.g. heat-shrinkable films). However, it is not a specific bulk property, but results from the polymer's structure and morphology. The effect is persistent in many polymers, which might differ significantly in their chemical composition. However only a few shape memory polymer systems have been described in the literature (Kim, et al., "Polyurethanes having shape memory effect," *Polymer* 37(26):5781–93 (1996); Li et al., "Crystallinity and morphology of segmented polyurethanes with different soft-segment length," *J. Applied Polymer* 62:631–38 (1996); Takahashi et al., "Structure and properties of shape-memory polyurethane block copolymers," *J. Applied Polymer Science* 60:1061–69 (1996); Tobushi H., et al., "Thermomechanical properties of shape memory polymers of polyurethane series and their applications," *J. Physique* IV (Colloque C1) 6:377–84 (1996)).

Examples of polymers used to prepare hard and soft segments of SMPs include various polyethers, polyacrylates, polyamides, polysiloxanes, polyurethanes, polyether amides, polyurethane/ureas, polyether esters, and urethane/butadiene copolymers. See, for example, U.S. Pat. No. 5,506,300 to Ward et al.; U.S. Pat. No. 5,145,935 to Hayashi; U.S. Pat. No. 5,665,822 to Bitler et al.; and Gorden, "Applications of Shape Memory Polyurethanes," *Proceedings of the First International Conference on Shape Memory and Superelastic Technologies, SMST International Committee*, pp. 115-19 (1994). The SMPs that have been developed thus far appear to be limited to being able to hold only one temporary shape in memory. It would be advantageous to provide SMPs that are able to form objects which are able to hold more than one shape in memory.

It is therefore an object of the present invention to provide SMPs that are able to form objects which are able to hold more than one shape in memory.

It is another object of the present invention to provide SMPs with physical and chemical properties and chemical structures which are different than those in conventional SMPs.

It is still another object of the present invention to provide SMPs with shapes in memory that are elicited by a stimulus other than temperature.

SUMMARY OF THE INVENTION

Shape memory polymer compositions, articles of manufacture thereof, and methods of preparation and use thereof are described. In a preferred embodiment, the shape memory polymer composition can hold more than one shape in memory. For example, the composition can include a hard segment and at least two soft segments. The $T_{trans}$ of the hard segment is at least 10° C., and preferably 20° C., higher than the $T_{trans}$ of one of the soft segments, and the $T_{trans}$ of each subsequent soft segment is at least 10° C., and preferably 20° C., lower than the $T_{trans}$ of the preceding soft segment. A multiblock copolymer with a hard segment with a relatively high $T_{trans}$ and a soft segment with a relatively low $T_{trans}$ can be mixed or blended with a second multiblock copolymer with a hard segment with a relatively low $T_{trans}$ and the same soft segment as that in the first multiblock copolymer. Since the soft segments in both multiblock copolymers are identical, the polymers are miscible in each other when the soft segments are melted. The resulting blend has three transition temperatures: one for the first hard segment, one for the second hard segment, and one for the soft segment. Accordingly, these materials are able to memorize two different shapes.

Any polymers that are crystalline or amorphous and that have a $T_{trans}$ within the range defined herein can be used to form the hard and soft segments. The melting point or glass transition temperature (hereinafter, the $T_{trans}$) of the hard segment is at least 10° C., and preferably 20° C., higher than the $T_{trans}$ of the soft segment. The $T_{trans}$ of the hard segment is preferably between −30 and 270° C., and more preferably between 30 and 150° C. The ratio by weight of the hard segment:soft segments is between about 5:95 and 95:5, preferably between 20:80 and 80:20.

In some embodiments, the shape memory polymers contain at least one physical crosslink (physical interaction of the hard segment) or contain covalent crosslinks instead of a hard segment. The shape memory polymers also can be interpenetrating networks or semi-interpenetrating networks. In addition to changes in state from a solid to liquid state (melting point or glass transition temperature), hard and soft segments may undergo solid to solid state transitions, and can undergo ionic interactions involving polyelectrolyte segments or supramolecular effects based on highly organized hydrogen bonds.

Articles of manufacture can be prepared from the shape memory polymer compositions, for example, by injection molding, blowing, extrusion, and laser ablation. To prepare an object having a shape in memory, the object can be formed at a temperature above the $T_{trans}$ of the hard segment, and cooled to a temperature below the $T_{trans}$ of the soft segment. If the object subsequently is formed into a second shape, the object can be returned to its original shape by heating the object above the $T_{trans}$ of the soft segment and below the $T_{trans}$ of the hard segment.

Articles of manufacture with two or more shapes in memory can be prepared by forming a polymer composition with a hard segment, a first soft segment, and a second soft segment, where the first soft segment has a $T_{trans}$ at least 10° C. below that of the hard segment and at least 10° C. above that of the second soft segment. After the composition is shaped at a temperature above the $T_{trans}$ of the hard segment, it can be cooled to a temperature below that of the $T_{trans}$ of the first soft segment and above that of the second soft segment and formed into a second shape. The composition can be formed into a third shape after it has been cooled below the $T_{trans}$ of the second soft segment. The composition can be heated above the $T_{trans}$ of the second soft segment to return the composition to the second shape. The composition can be heated above the $T_{trans}$ of the first soft segment to return the composition to the first shape. The composition can also be heated above the $T_{trans}$ of the hard segment, at which point the composition loses the memory of the first and second shapes and can be reshaped using the method described above.

Thermoset polymers can be prepared by pre-shaping macromonomers, for example, by extrusion, and fixing the original shape at a temperature above the $T_{trans}$ of the thermoset polymer, for example, by photocuring reactive groups on the macromonomer. The original shape, however, can only be programmed one time.

In a preferred embodiment, the shape change occurs in response to a change in temperature. In another embodiment, however, the composition can change its shape in response to application of light, changes in ionic concentration and/or pH, electric field, magnetic field or ultrasound. For example, a SMP can include at least one hard segment and at least one soft segment, wherein at least two of the segments, preferably two soft segments, are linked to each other via a functional group that is cleavable under application of light, electric field, magnetic field or ultrasound. The temporary shape is fixed by crosslinking the linear polymers. By cleaving those links the original shape can be recovered. The stimuli for crosslinking and cleaving these bonds can be the same or different.

DETAILED DESCRIPTION OF THE INVENTION

Figure 1:
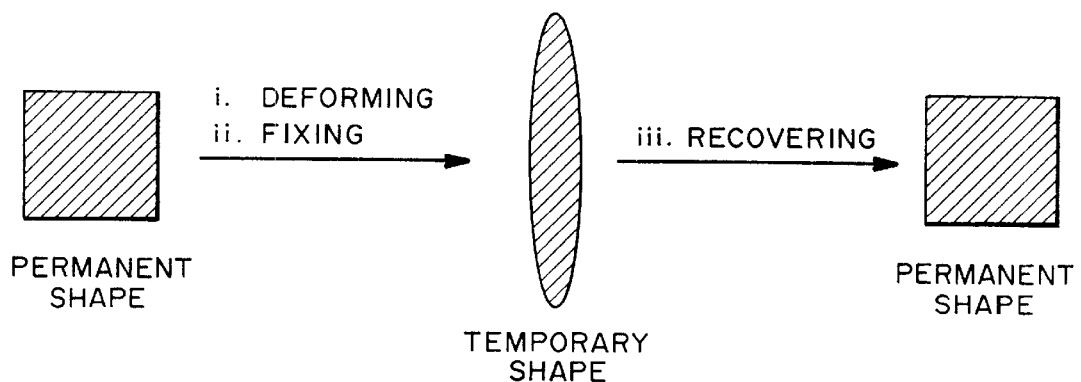
FIG. 1 is an illustration of the one-way shape memory effect.
Figure 2:
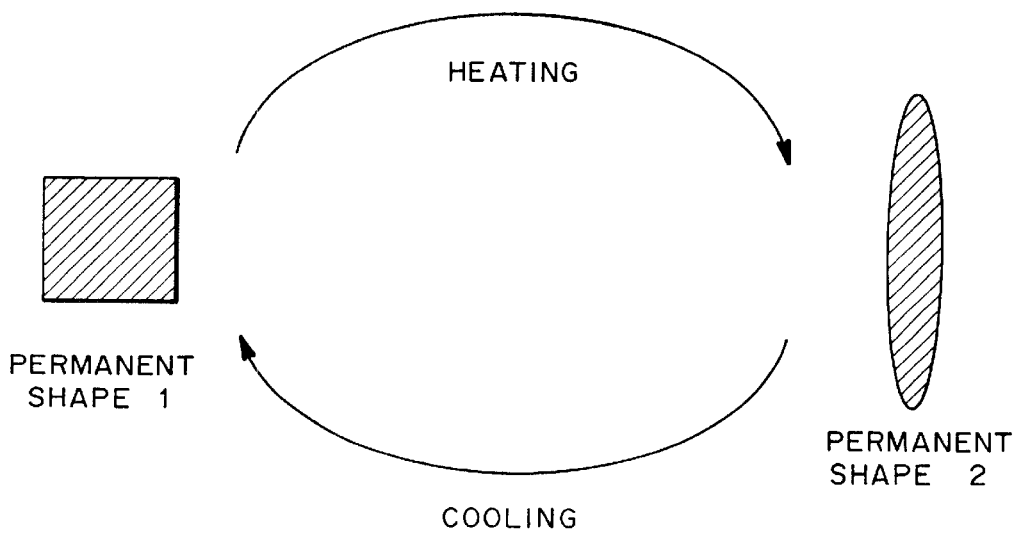
FIG. 2 is an illustration of the two-way (thermal) shape memory effect.

Shape memory polymer compositions, articles of manufacture thereof, and methods of preparation and use thereof are provided. The shape memory polymers can include at least one hard segment and at least one soft segment, or can include at least one kind of soft segment wherein at least one kind of the soft segments are crosslinked, without the presence of a hard segment. In a preferred embodiment, the polymers can hold two or more shapes in memory.

Definitions

A polymer is a shape memory polymer if the original shape of the polymer is recovered by heating it above a shape recovering temperature (defined as the $T_{trans}$ of a soft segment) even if the original molded shape of the polymer is destroyed mechanically at a lower temperature than the shape recovering temperature, or if the memorized shape is recoverable by application of another stimulus.

As used herein, the term "segment" refers to a block or sequence of polymer forming part of the shape memory polymer.

As used herein, the terms hard segment and soft segment are relative terms, relating to the $T_{trans}$ of the segments. The hard segment(s) has a higher $T_{trans}$ than the soft segment(s). The ratio by weight of the hard segment:soft segments is between about 5:95 and 95:5, preferably between 20:80 and 80:20.

As used herein, the term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used herein in reference to polymers, the term "degrade" refers to cleavage of the polymer chain, such that the molecular weight stays approximately constant at the oligomer level and particles of polymer remain following degradation. The term "completely degrade" refers to cleavage of the polymer at the molecular level such that there is essentially complete mass loss. The term "degrade" as used herein includes "completely degrade" unless otherwise indicated.

Shape Memory Polymer Compositions

Shape memory polymers can be thermoplastic, thermoset, interpenetrating networks, semi-interpenetrating networks, or mixed networks. Polymers can be a single polymer or a blend of polymers. Polymers can be linear, branched, thermoplastic elastomers with side chains or any kind of dendritic structural elements. Stimuli causing shape change can be temperature, ionic change, pH, light, electric field, magnetic field or ultrasound.

Thermoplastic shape memory materials can be shaped (e.g. molded) to a desired shape above the $T_{trans}$ of the hard segment(s) and cooled to a temperature below the shape recovering temperature, where the polymer may undergo mechanical deformation, and strains are generated in the polymer. The original shape of the deformed polymers can be recovered by heating them to a temperature higher than their shape recovering temperature. Above this temperature, the strains in the polymer are relieved, allowing the polymer to return to its original shape. In contrast, thermoset shape memory materials are shaped to a desired shape before the macromonomers used to form the thermoset polymers are polymerized. After the shape has been fixed, the macromonomers then are polymerized.

The polymer compositions are preferably compressible by at least one percent or expandable by at least five one of the original thickness at a temperature below the shape recovering temperature, with the deformation being fixed by application of a stimulus such as heat, light, ultrasound, magnetic fields or electric fields. In some embodiments, the materials show a ratio of recovery of 98% (compare to experimental examples).

When significant stress is applied, resulting in an enforced mechanical deformation at a temperature lower than the shape recovering temperature, strains are retained in the soft segments, or amorphous regions, and bulky shape change is kept even after the partial liberation of strain by the elasticity of the polymer. If the configuration of the molecular chains is disturbed by influencing the regulated arrangement of molecular chains at a temperature lower than the glass transition temperature, rearrangement of the molecular chains is assumed to occur through the increase of the volume size and the decrease of the free volume content. The original shape is recovered by the contraction of the hard segment aggregates by the elevation of the temperature according to rigid control of chain conformations and the shape of the polymer is restored to the memorized shape.

In addition to changes in state from a solid to liquid state (melting point or glass transition temperature), hard or soft segments can undergo ionic interactions involving polyelectrolyte segments or supramolecular effects based on highly organized hydrogen bonds. The SMP may undergo solid state to solid state transitions (e.g. a change in morphology). Solid state to solid state transitions are well known to those of skill in the art, for example as in poly(styrene-block-butadiene).

An object formed using shape memory polymers can be prepared to control the direction of change during recovery. In other words, contraction and/or expansion can occur along one or more dimensional axes depending how the polymers are shaped and stressed. For example, in a SMP fiber, the change in shape can be limited to one dimension, such as along the length.

In another embodiment, the thermal and electrical conductivity of the SMP materials can be changed in response to changes in temperature.

The moisture permeability of the compositions can be varied, especially when the polymer is formed into a thin film (i.e., less than about 10 $\mu$m). Some polymer compositions, in their original shape, have a sufficient permeability such that molecules of water vapor can be transmitted through the polymer film, while water molecules are not large enough to penetrate the polymer film. The resulting materials have low moisture permeability at temperatures below room temperature and high moisture permeability at temperatures above room temperature.

I. Polymer Segments

The polymers incorporate "hard" and "soft" segments. The segments preferably are oligomers. As used herein, the term "oligomer" refers to a linear chain molecule having a molecular weight up to 15,000 Daltons. The polymers forming the segments are selected based on the desired glass transition temperature(s) (if at least one segment is amorphous) or the melting point(s) (if at least one segment is crystalline), which in turn is based on the desired applications, taking into consideration the environment of use. Preferably, the number average molecular weight of the polymer segment is greater than 400, and is preferably in the range of between 500 and 15,000.

The transition temperature at which the polymer abruptly becomes soft and deforms can be controlled by changing the monomer composition and the kind of monomer, which enables one to adjust the shape memory effect at a desired temperature. The thermal properties of the polymers can be detected, for example, by dynamic mechanical thermoanalysis or differential scanning calorimetry (DSC) studies. In addition the melting point can be determined using a standard melting point apparatus.

The polymers can be thermoset or thermoplastic polymers, although thermoplastic polymers may be preferred due to their ease of molding. Thermosets, however, may be preferred in some applications, since they generally are softer than physically crosslinked polymer in their original shape at temperatures greater than $T_{trans}$.

Preferably, the degree of crystallinity of the polymer or polymeric block(s) is between 3 and 80%, more preferably between 3 and 60%. When the degree of crystallinity is greater than 80% while all soft segments are amorphous, the resulting polymer composition has poor shape memory characteristics.

The tensile modulus of the polymers below the $T_{trans}$ is typically between 50 MPa and 2 GPa (gigapascals), whereas the tensile modulus of the polymers above the $T_{trans}$ is typically between 1 and 500 MPa. Preferably, the ratio of elastic modulus above and below the $T_{trans}$ is 20 or more. The higher the ratio, the better the shape memory of the resulting polymer composition.

The polymer segments can be natural or synthetic, although synthetic polymers are preferred. The polymer segments can be biodegradable or non-biodegradable, although biodegradable polymer compositions generally are preferred for in vivo medical applications. In general, these materials degrade by hydrolysis, by exposure to water or enzymes under physiological conditions, by surface erosion, by bulk erosion, or a combination thereof Non-biodegradable polymers used for medical applications preferably do not include aromatic groups, other than those present in naturally occurring amino acids.

The polymers are selected based on the desired glass transition temperature(s) (if at least one segment is amorphous) or the melting point(s) (if at least one segment is crystalline), which in turn is based on the desired applications, taking into consideration the environment of use. Preferably, the number average molecular weight of the polymer block is greater than 400, and is preferably in the range of between 500 and 15,000.

The polymer may be in the form of a hydrogel (typically absorbing up to about 90% by weight of water), and can optionally be ionically crosslinked with multivalent ions or polymers. Ionic crosslinking between soft segments can be used to hold a structure, which, when deformed, can be reformed by breaking the ionic crosslinks between the soft segments. The polymer may also be in the form of a gel in solvents other than water or aqueous solutions. In these polymers, the temporary shape can be fixed by hydrophilic interactions between soft segments.

Representative natural polymer blocks or polymers include proteins such as zein, modified zein, casein, gelatin, gluten, serum albumin, and collagen, and polysaccharides such as alginate, celluloses, dextrans, pullulane, and polyhyaluronic acid, as well as chitin, poly(3-hydroxyalkanoate)s, especially poly($\beta$-hydroxybutyrate), poly(3-hydroxyoctanoate) and poly(3-hydroxyfatty acids). Representative natural biodegradable polymer blocks or polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers.

Representative synthetic polymer blocks or polymers include polyphosphazenes, poly(vinyl alcohols), polyamides, polyester amides, poly(amino acid)s, synthetic poly(amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polynrethanes and copolymers thereof. Examples of suitable polyacrylates include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate).

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt. These are collectively referred to herein as "celluloses".

Representative synthetic degradable polymer segments include polyhydroxy acids, such as polylactides, polyglycolides and copolymers thereof; poly(ethylene terephthalate); polyanhydrides, poly(hydroxybutyric acid); poly(hydroxyvaleric acid); poly[lactide-co-(s-caprolactone)]; poly[glycolide-co-(s-caprolactone)]; polycarbonates, poly(pseudo amino acids); poly(amino acids); poly(hydroxyalkanoate)s; polyanhydrides; polyortho esters; and blends and copolymers thereof. Polymers containing labile bonds, such as polyanhydrides and polyesters, are well known for their hydrolytic reactivity. Their hydrolytic degradation rates can generally be altered by simple changes in the polymer backbone and their sequence structure.

Examples of non-biodegradable synthetic polymer segments include ethylene vinyl acetate, poly(meth)acrylic acid, polyamides, polyethylene, polypropylene, polystyrene, polyvinyl chloride, polyvinylphenol, and copolymers and mixtures thereof.

The polymers can be obtained from commercial sources such as Sigma Chemical Co., St. Louis, Mo.; Polysciences, Warrenton, Pa; Aldrich Chemical Co., Milwaukee, Wis.; Fluka, Ronkonkoma, N.Y.; and BioRad, Richmond, Calif. Alternately, the polymers can be synthesized from monomers obtained from commercial sources, using standard techniques.

Hydrogels

Hydrogels can be formed from polyethylene glycol, polyethylene oxide, polyvinyl alcohol, polyvinyl pyrrolidone, polyacrylates, poly (ethylene terephthalate), poly(vinyl acetate), and copolymers and blends thereof. Several polymeric blocks, for example, acrylic acid, are elastomeric only when the polymer is hydrated and hydrogels are formed. Other polymeric blocks, for example, methacrylic acid, are crystalline and capable of melting even when the polymers are not hydrated. Either type of polymeric block can be used, depending on the desired application and conditions of use.

For example, shape memory is observed for acrylic acid copolymers only in the hydrogel state, because the acrylic acid units are substantially hydrated and behave like a soft elastomer with a very low glass transition temperature. The dry polymers are not shape memory polymers. When dry, the acrylic acid units behave as a hard plastic even above the glass transition temperature and show no abrupt change in mechanical properties on heating. In contrast, copolymers including methyl acrylate polymeric blocks as the soft segments show shape memory properties even when dry.

Certain polymers, for example, poly(ethylene oxide-co-propylene oxide) block copolymers (PLURONICS™, BASF) are soluble in water at temperatures lower than body temperature and become hydrogels at temperatures higher than body temperature. Incorporation of these polymers as blocks in shape memory polymers provides the shape memory polymers with the ability to response to changes in temperature in a manner totally opposite that of typical shape memory polymers. These materials recover their shape when cooled below their shape recovery temperature, rather than being heated above their shape recovery temperature. This effect is called inversed thermal shape memory effect. Shape memory polymer compositions including these polymer blocks are useful in various biomedical applications where the polymer can be inserted as a liquid, and cooled to recover an intended shape in situ. The inverse thermal shape memory effect can be obtained by incorporating two different blocks into a polymer that are miscible at temperatures lower than $T_{misc}$ but are immiscible at higher temperatures. The phase separation at higher temperatures stabilizes the temporary shape.

Various polymers, such as polyacetylene and polypyrrole, are conducting polymers. These materials are particularly preferred for uses in which electrical conductance is important. Examples of these uses include tissue engineering and any biomedical application where cell growth is to be stimulated. These materials may find particular utility in the field of computer science, as they are able to absorb heat without increasing in temperature better than SMAs. Conducting shape memory polymers are useful in the field of tissue engineering to stimulate the growth of tissue, for example nerve tissue.

II. Assembly of Polymer Segments

In a preferred embodiment, the shape memory polymer composition is able to hold more than one shape in memory. For example, the composition can include a hard segment and at least two soft segments, wherein the $T_{trans}$ of the hard segment is between −30 and 270° C., and is at least 10° C., and preferably 20° C., higher than the $T_{trans}$ of one of the soft segments, and the $T_{trans}$ of each subsequent soft segment is at least 10° C., and preferably 20° C., lower than the $T_{trans}$ of the preceding soft segment. Optionally, one or more of the segments can be biodegradable or linked to another segment via a biodegradable linkage, such as ester-, amide-, anhydride-, carbonate-, or orthoester linkages.

The shape memory effect is based on the polymer morphology. With respect to thermoplastic elastomers, the original shape of an object is fixed by physical crosslinks caused by the hard segment. With respect to thermoset polymers, the soft segments are covalently crosslinked instead of having hard segments. The original shape is set by the crosslinking process.

In contrast to prior art segmented polyurethane SMPs, the segments of the compositions described herein need not be linear. The segments can be partially grafted or attached in dendremeric side groups.

Thermoplastic and Thermoset Polymers

Figure 3:
FIG. 3 is an illustration of combinations of suitable classes of thermoplastic materials.
Figure 3:
Figure 3:
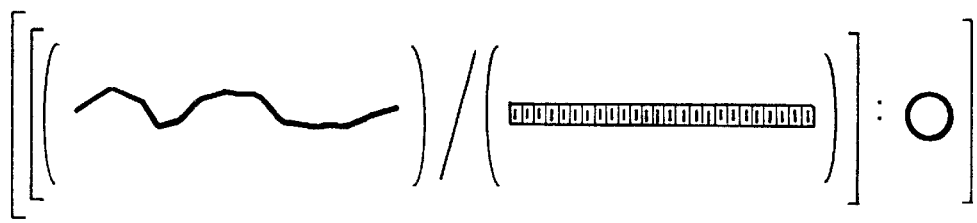
Figure 3:
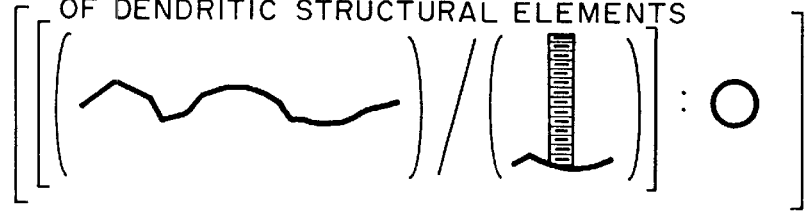
Figure 3:
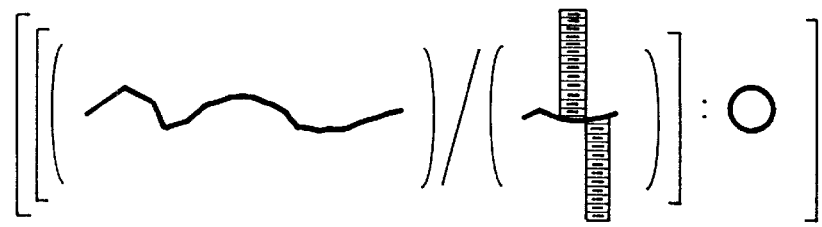
Figure 3:
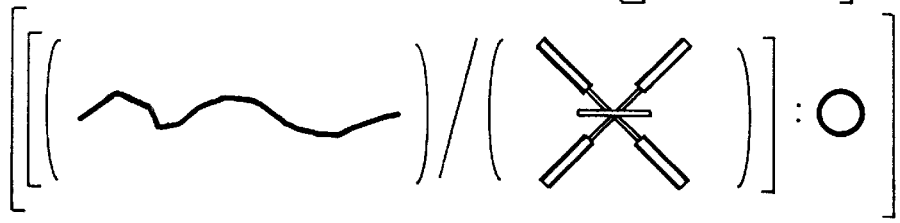

The polymers can be in the form of linear diblock-, triblock-, tetrablock, or multiblock copolymers, branch or graft polymers, thermoplastic elastomers, which contain dendritic structures, and blends thereof. FIG. 3 illustrates some of the combinations of suitable classes of thermoplastic materials forming the hard and soft segments. The thermoplastic shape memory polymer composition also can be a blend of one or more homo- or co-polymer with one or more diblock-, triblock-, tetrablock, or multiblock copolymers, branch or graft polymers. These types of polymers are well known to those of skill in the art.

The polymers can be thermoset polymers. There are four different types of thermoset polymers that have shape memory capability. These include polymer networks, semi-interpenetrating networks, interpenetrating networks, and mixed-interpenetrating networks.

i. Polymer Networks

A polymer network is prepared by covalently crosslinking macromonomers, i.e., polymers which contain polymerizable endgroups such as carbon-carbon double bonds. The polymerization process can be induced by using light or heat sensitive initiators or by curing with ultraviolet light ("UV-light") without an initiator. Shape memory polymer networks are prepared by crosslinking one or more soft segments which correspond to one or more thermal transitions.

Figure 4:
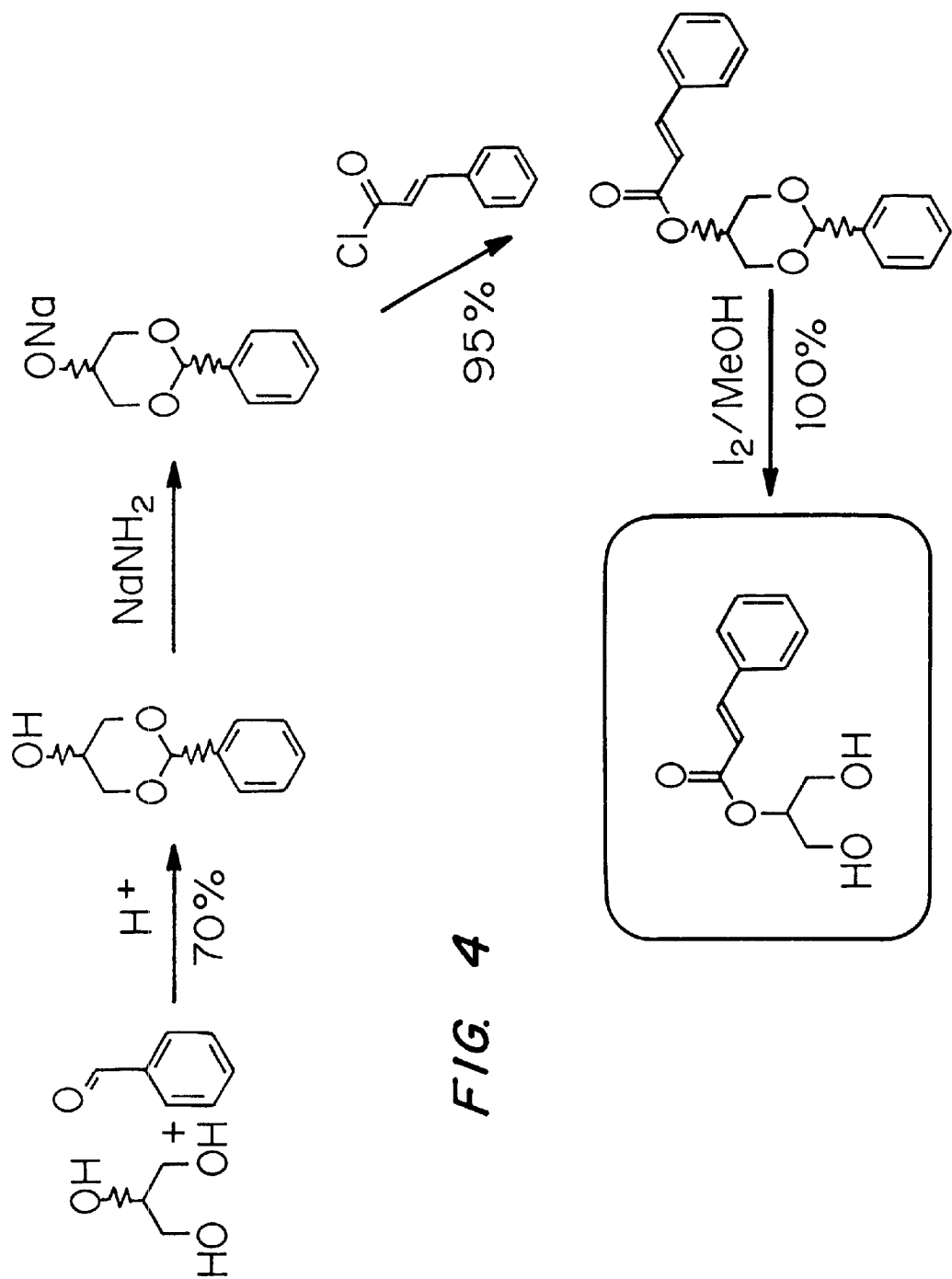
FIG. 4 is a diagram of a reaction sequence for the synthesis of a preferred photocrosslinker.
Figure 5:
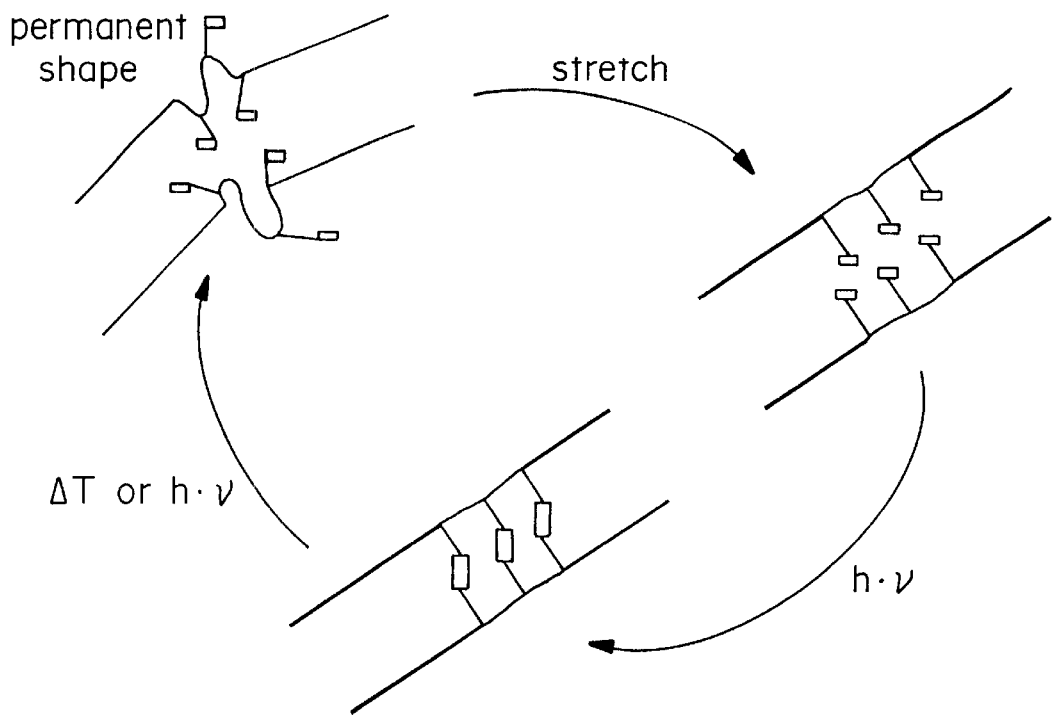
FIG. 5 is an illustration of a photoinduced shape memory effect.

In an embodiment preferred for biomedical applications, the crosslinking is performed using a photocrosslinker and requires no chemical initiator. The photocrosslinker advantageously eliminates the need for initiator molecules, which may be toxic. FIG. 4 is a diagram of a reaction sequence for the synthesis of a preferred photocrosslinker, which produced an overall yield of about 65%.

ii. Interpenetrating Networks

Interpenetrating networks ("IPN") are defined as networks where two components are crosslinked, but not to each other. The original shape is determined by the network with the highest crosslink density and the highest mechanical strength. The material has at least two $T_{trans}$ corresponding to the different soft segments of both networks.

iii. Mixed.Interpenetrating Network

A mixed IPN includes at least one physically crosslinked polymer network (a thermoplastic polymer) and at least one covalently crosslinked polymer network (a thermoset polymer) that cannot be separated by any physical methods. The original shape is set by the covalently crosslinked network. The temporary shapes correspond to the $T_{trans}$ of the soft segments and the $T_{trans}$ of the hard segment of the thermoplastic elastomer component.

A particularly preferred mixed interpenetrating network is prepared by polymerizing a reactive macromonomer in the presence of a thermoplastic polymer, for example, by the photopolymerization of carbon-carbon double bonds. In this embodiment, the ratio by weight of thermoset polymer to thermoplastic polymer is preferably between 5:95 and 95:5, more preferably, between 20:80 and 80:20.

iv. Semi-Interpenetrating Networks

Semi-interpenetrating networks ("semi-IPN") are defined as two independent components, where one component is a crosslinked polymer (a polymer network) and the other component is a non-crosslinked polymer (a homopolymer or copolymer), wherein the components cannot be separated by physical methods. The semi-IPN has at least one thermal transition corresponding to the soft segment(s) and the homo- or co-polymer components. The crosslinked polymer preferably constitutes between about 10 and 90% by weight of the semi-interpenetrating network composition.

v. Polymer Blends

The shape memory polymers can exist as physical mixtures of thermoplastic polymers. In one embodiment, a shape memory polymer composition can be prepared by interacting or blending two thermoplastic polymers. The polymers can be semicrystalline homopolymers, semicrystalline copolymers, thermoplastic elastomers with linear chains, thermoplastic elastomers with side chains or any kind of dendritic structural elements, and branched copolymers, and these can be blended in any combination thereof.

For example, a multiblock copolymer with a hard segment with a relatively high $T_{trans}$ and a soft segment with a relatively low $T_{trans}$ can be mixed or blended with a second multiblock copolymer with a hard segment with a relatively low $T_{trans}$ and the same soft segment as that in the first multiblock copolymer. The soft segments in both multiblock copolymers are identical, so the polymers are miscible in each other when the soft segments are melted. There are three transition temperatures in the resulting blend –that of the first hard segment, that of the second hard segment, and that of the soft segment. Accordingly, these materials are able to memorize two different shapes. The mechanical properties of these polymers can be adjusted by the changing the weight ratio of the two polymers.

Other kinds of blends of at least two multiblock copolymers, in which at least one of the segments is miscible with at least one of the segments of the other multiblock copolymers, can be prepared. If two different segments are miscible and build one domain together, then the thermal transition of this domain depends on the weight content of the two segments. The maximum number of memorized shapes results from the number of thermal transitions of the blend.

Shape memory blends may have better shape memory capabilities than the blend components alone. Shape memory blends are composed of at least one multiblock copolymer and at least one homo- or copolymer. Di-, tri-, or tetra-block copolymers should be suitable substitutes for a multiblock copolymer.

Shape memory blends are highly useful in industrial applications, since a broad range of mechanical, thermal, and shape memory capabilities can be obtained from only two or three basic polymers by blending them in different weight ratios. A twin screw extruder is an example of standard process equipment that could be used to mix the components and process the blend.

Polymers with Functional Groups Which Respond to Stimuli Other Than Temperature

In a preferred embodiment, the shape memory polymeric composition includes at least one hard segment and at least one soft segment or multiple soft segments that are covalently crosslinked, wherein at least two of the segments are linked via a functional group which is cleavable under application of light, changes in ionic concentration, changes in pH, electric field, magnetic field, and/or ultrasound. In addition to changing shape in response to changes in temperature, the composition can change its shape in response to application of light, changes in ionic concentration, changes in pH, electric field, magnetic field and/or ultrasound. The temporary shape in these polymers is fixed by the covalent crosslinks.

i. Photochemical Stimuli

Photoreversible reactions can be used to link soft segments together and hold the polymer in a temporary shape. The original shape of a material is set by the hard segment. Upon photochemical cleavage of these linkages, the material returns to its original shape. As these reactions are photoreversible, the bonds can be made and broken through several cycles. However, each time the bonds are broken, they need to be remade in order to memorize the shape. Examples of such functional groups capable of undergoing photoreversible reactions are cinnamon acid derivatives and cinnamylidene acid derivatives. Linking and cleavage can be induced by different wavelengths of UV-light. In addition cleavage can occur during a thermal treatment.

In another embodiment, the polymers can include side chains with chromophores, such as azo- groups, that absorb light. The chromophores also may be incorporated into the main chain. The hard and/or soft segments can also include double bonds that shift from cis to trans isomers when the chromophores absorb light. Light can therefore be used to isomerize the segment, which can dramatically affect the $T_{trans}$ of the segment. The original shape of such polymers is set by the hard segment. The polymer then can be deformed into a temporary shape. The temporary shape can be fixed by curing the polymer with light to cause photoisomerization. In this way, the polymer is hindered from returning to its original shape, because the thermal transition temperature has been increased. Solid to solid phase transitions also may be induced in this manner.

ii. Changes in Ionic Strength and/or pH

Various functional groups are known to crosslink in the presence of certain ions or in response to changes in pH. For example, calcium ions are known to crosslink amine and alcohol groups, i.e., the amine groups on alginate can be crosslinked with calcium ions. Also, carboxylate and amine groups become charged species at certain pHs. When these species are charged, they can crosslink with ions of the opposite charge. The presence of groups which respond to changes in the concentration of an ionic species and/or to changes in pH on hard and/or soft segments results in reversible linkages between these segments. One can fix the shape of an object while crosslinking the segments. After the shape has been deformed, alteration of the ionic concentration or pH can result in cleavage of the ionic interactions which formed the crosslinks between the segments, thereby relieving the strain caused by the deformation and thus returning the object to its original shape. Because ionic bonds are made and broken in this process, it can only be per-formed once. The bonds, however, can be re-formed by altering the ionic concentration and/or pH, so the process can be repeated as desired.

iii. Electric and Magnetic Fields

Various moieties, such as chromophores with a large number of delocalized electrons, increase in temperature in response to pulses of applied electric or magnetic fields as a result of the increased electron flow caused by the fields. After the materials increase in temperature, they can undergo temperature induced shape memory in the same manner as if the materials were heated directly. These compositions are particularly useful in biomedical applications where the direct application of heat to an implanted material may be difficult, but the application of an applied magnetic or electric field would only affect those molecules with the chromophore, and not heat the surrounding tissue.

iv. Ultrasound

Various materials contain reactive functional groups which fragment in response to applied ultrasound. Examples of these groups are those which form stable radicals, such as nitroso and triphenylmethane groups. One can fix the shape of an object while forming bonds between two or more soft segments, for example by using heat or light. After the shape is deformed, the application of ultrasound can break the bonds between the soft segments, and relieve the strain caused by the deformation. The object will then return to its original shape. Because covalent bonds are made and broken in this process, it can only be performed once.

III. Methods of Making the Polymers

The polymer used to form the segments in the SMPs described above are either commercially available or can be synthesized using routine chemistry. Those of skill in the art can readily prepare the polymers using known chemistry.

IV. Methods of Shaping the Polymer Compositions

The compositions can be formed into a first shape under appropriate conditions, for example, at a temperature above the $T_{trans}$ of the hard segments, and allowed to cool below the $T_{trans}$ of the soft segment(s). Standard techniques are extrusion and injection molding. Optionally, the object can be re-formed into a second shape. Upon application of heat or other appropriate set of conditions, the object returns to original shape.

Thermoset polymers can be prepared by extruding the pre-polymerized material (macromonomers), and fixing the original shape at a temperature above the $T_{trans}$ of the thermoset polymer, for example, by photocuring reactive groups on the monomer. The temporary shape is fixed by cooling the material below $T_{trans}$ after deforming the material.

The crosslinking also can be performed in a solution of the macromonomers. The solvent is removed from the formed gel in a subsequent step.

Those compositions formed of thermoplastic polymers can be blown, extruded into sheets or shaped by injection molding, for example, to form fibers. The compositions can also be shaped by other methods known to those of skill in the art for shaping solid objects, for example, laser ablation, micromachining, use of a hot wire, and by CAD/CAM (computer aided design/computer aided manufacture) processes. These processes are preferred for shaping thermoset polymers.

1. Transitions Among Shapes

For several applications it is advantageous to go in small steps from a temporary shape to another temporary shape or the original shape. It is possible to go back and forth between shapes as needed, under the control of an operator.

A. Broad Thermal Transitions

Usually the $T_{trans}$ of a shape memory polymer is sharp, so that the polymer will recover its original shape simply by heating the material only a few degree Celsius. In an alternate embodiment, however, the shape memory polymer has a broad thermal transition, such that the original shape is fully recovered only when the polymer is heated higher than the upper limit of the thermal transition. A partial recovery will occur when heating at a temperature between the lower and the upper limits of the thermal transition. In this embodiment, the trigger is the temperature, and the effect is essentially independent of the time interval of heat application.

B. Stepwise Energy Transfer

A certain amount of energy needs to be transferred to the shape memory polymer in order to recover a memorized shape. For the thermal shape memory effect, the amount of energy required to fully recover a memorized shape depends on the heat capacity of the material. For light sensitive materials, however, the amount of energy depends on the dosage of irradiation. In a preferred embodiment of a thermal shape memory effect, the polymer has a sharp thermal transition, which is triggered based on the duration the material is exposed to a temperature greater than Trans. Other factors affecting the transition include the mass or size of the material, and the temperature and heat transfer coefficient of the medium or environment in contact with (and used to heat) the material. For example, the higher the temperature of the environment, the more quickly the memorized shape is recovered.

C. Selective Energy Transfer and Alternative Mechanisms

In case of the classical thermal shape memory effect, the entire polymer must be heated by application (and transfer) of heat energy from an external source in order to recover the original shape. In an alternate embodiment, the polymer is heated by energy sources other than temperature. Using these techniques it is possible not only to heat the whole shape memory device, but also selective parts of the shape memory device (another way of triggering and enhancing control to recover the original shape)

i. Light Energy

Polymers absorb light at different wavelengths, depending on their chemical structure. Polymers typically show strong absorption of radiation in the infrared (IR) and near-infrared (NIR) region. The strongest and most suitable absorption ranges for a particular polymer application can be identified using IR or NIR spectroscopy. Shape memory polymers also can show strong absorption in the ultraviolet (UV) region. The polymer can be cured with light including at least one of the specified frequencies in its spectra, such that the polymer will absorb the light energy and heat up.

The absorption characteristics of the shape memory polymer can be modified by the addition of a chromophor, which is a moiety, functional group, or molecule showing strong absorption in specific regions of the UV/visible/IR/NIR microwave spectrum. The chromophor can be covalently bound to the polymer, combined as a physical mixture with the polymer, or both.

In a preferred biomedical embodiment, light can be used to noninvasively control an implanted SMP device. For example, the implanted polymer can be cured using specific external light sources that do not simultaneously heat tissue, serum, or other parts of the physiological environment surrounding the SMP implant. Such a light source (e.g., lamp) should emit one or more frequencies of light (e.g., near infrared, "NR") that are not absorbed by the physiological environment, but which are absorbed by the shape memory material. The use of NIR light is known in the diagnostics art.

In an alternate embodiment, the technique of interference is applied to control the light frequency applied to an implanted SMP. Interference provides three-dimensional (3-D) control of the region being cured, as the specific frequency of light being absorbed by the shape memory device is produced at a specified location by the interference of two or more beams crossed at the specified location. The sources of the beams are outside the body, and the frequencies of the beams generally are modulated radio frequencies selected to produce the desired application frequency from the resulting interference.

ii. Ultrasound

In an alternate embodiment, gas bubbles or bubble containing liquids, preferably fluorocarbons, are incorporated in the shape memory device. Using standard ultrasound technology, one can induce a cavitation effect in the gas/liquid to heat the SMP. Techniques for 3-D controlled application of ultrasound are known in the art of biomedical diagnostics.

iii. General

It is also possible to effect energy transfers based on the interaction of the shape memory polymer and electromagnetic fields. The use of electromagnetic fields to induce heating or localized temperature changes are well known. In yet another embodiment, energy transfer is produced based on non-radiation effects, such as Foerster-Perrin energy transfer.

2. Two-Way Shape Memory Effect

Shape memory polymer compositions can be prepared to have two original (permanent) shapes, i.e. a two-way shape memory effect. These systems always consist of at least two components. The components are combined by layer techniques (similarly to bimetals) or are interpenetrating networks. By changing the temperature, the shape memory device changes its shape in the direction of permanent shape 1 or permanent shape 2. Each of the permanent shapes belongs to one component of the device. The shapes of the device always are in equilibrium between both shapes. The temperature dependence of the shape is caused by the fact that the mechanical properties of one component ("component A") are almost independent from the temperature in the temperature interval of interest. The mechanical properties of the other component ("component B") depend on the temperature. In one embodiment, component B becomes stronger at low temperatures compared to component A, while component A is stronger at high temperatures and determines the actual shape. A two-way memory device can be prepared by (a) setting the original shape of component A; (b) deforming the device into original shape of component B; and (c) fixing an original shape of component B while applying a stress to the component.

3. Initiation of Original Shape Recovery by Polymer Degradation

The recovery of the original shape of a shape memory polymer can be initiated by a hydrolytic degradation process. In a preferred embodiment, this feature is incorporated into a system including a thermoplastic polymer composed of a hard segment and at least one soft segment or a thermoset containing at least one soft segment (single component systems). In these polymers, two soft segments can be linked by an readily hydrolyzable bond. The term "readily hydrolyzable bond" is used herein to refer to groups having a hydrolysis rate that is greater than that for other functional groups in the polymer. The original shape of these polymers is determined by the hard segments (thermoplastic material) or the covalent crosslinks (thermoset). The temporary shape is fixed by the crosslinks between two soft segments after deforming the device. When the crosslinks between the soft segment are hydrolyzed, the original shape will be recovered. Readily hydrolyzable functional groups include activated ester bonds, such as glycolyl glycolate, and anhydride bonds.

In another preferred embodiment, the polymer is a two component system, in which at least one component is a covalent network, such as an IPN, a mixed-IPN, or a semi-IPN. The covalent network is an amorphous network having a very low $T_{trans}$. The covalent network determines the original shape of the system, and the second component deforms the system to fix the temporary shape. The second component is another network in the case of an IPN, a homo- or co-polymer in the case of a semi-IPN, and a thermoplastic elastomer in the case of a mixed-IPN. The first component (covalent network) hydrolyzes more slowly than the second component, such that the polymer recovers its original shape when the second component is degraded.

V. Applications

These materials have an enormous number of applications.

1. Therapeutic, Prophylactic, and Diagnostic Applications

These materials are particularly useful in medical and biological applications.

For example, any of a variety of therapeutic, prophylactic and/or diagnostic agents can be incorporated within the polymer compositions, which can locally or systemically deliver the incorporated agents following administration to a patient. Representative examples include synthetic inorganic and organic compounds or molecules, proteins and peptides, polysaccharides and other sugars, lipids, and nucleic acid molecules having therapeutic, prophylactic or diagnostic activities. Nucleic acid molecules include genes, plasmid DNA, naked DNA, antisense molecules which bind to complementary DNA to inhibit transcription, ribozymes and ribozyme guide sequences. The agents to be incorporated can have a variety of biological activities, such as vasoactive agents, neuroactive agents, hormones, growth factors, cytokines, anaesthetics, steroids, anticoagulants, anti-inflammatories, immunomodulating agents, cytotoxic agents, prophylactic agents, antibiotics, antivirals, antisense, antigens, and antibodies. In some instances, the proteins may be antibodies or antigens which otherwise would have to be administered by injection to elicit an appropriate response. Proteins are defined as consisting of 100 amino acid residues or more; peptides are less than 100 amino acid residues. Unless otherwise stated, the term protein refers to both proteins and peptides. Polysaccharides, such as heparin, can also be administered. Compounds with a wide range of molecular weight, for example, between 10 and 500,000 grams per mole, can be encapsulated.

Diagnostic or imaging agents which may be utilized include commercially available agents used in positron emission tomography (PET), computer assisted tomography (CAT), single photon emission computerized tomography, x-ray, fluoroscopy, magnetic resonance imaging (MRI), and ultrasound contrast agents.

2. Articles and Devices for Biomedical Applications

The polymer compositions can be used to prepare articles of manufacture for use in biomedical applications. For example, sutures, orthodontic materials, bone screws, nails, plates, meshes, prosthetics, pumps, catheters, tubes, films, stents, orthopedic braces, splints, tape for preparing casts, and scaffolds for tissue engineering, contact lenses, drug delivery devices, implants, and thermal indicators, can be prepared.

Implantable polymer compositions are preferably prepared from biocompatible polymers, and, for most applications, from biodegradable polymers. Biodegradable polymers degrade at a controlled rate depending on the composition and crosslinking of the polymer. Degradable polymeric implants eliminate the need for implant retrieval and can be used simultaneously to deliver therapeutic agents. The materials can be used in many applications requiring load-bearing capacities and controlled degradation.

The polymer compositions can be formed into the shape of an implant which can be implanted within the body to serve a mechanical function. Examples of such implants include rods, pins, screws, plates and anatomical shapes. A particularly preferred use of the compositions is to prepare sutures that have a rigid enough composition to provide for ease of insertion, but upon attaining body temperature, soften and form a second shape that is more comfortable for the patient while still allowing healing.

Another preferred use is in the area of catheters. Catheters generally require high stiffness for insertion, but once inserted a soft, flexible catheter is preferred. In a preferred embodiment, the SMP catheter is rigid below body temperature for ease of insertion, and after warming to body temperature becomes soft to reduce patient discomfort and complications.

The polymer compositions can be combined with fillers, reinforcement materials, radioimaging materials, excipients or other materials as needed for a particular implant application. Those of skill in the art can readily determine a suitable amount of these materials to include in the compositions.

The articles can incorporate various therapeutic and/or diagnostic agents, as described above.

3. Non-Medical Applications

There are numerous applications for the shape memory polymer compositions other than biomedical applications.

These applications include: shape memory polymer foams, members requiring deformation restoration after impact absorption, such as bumpers and other autobody parts, packaging for foodstuffs, automatic chokes for internal combustion engines, polymer composites, textiles, humidity permeable clothes, such as sportswear, diapers and shoe inner lining materials, pipe joints, mask core materials, heat shrinkable tubes, re-writable compact discs (CDs) and clamping pins, temperature sensors, damping materials, footbed and protective equipment, toys, bonding materials for singular pipes internal laminating materials of pipes, lining materials, clamping pins, medical instrument materials such as gyps, etc., stationary and educational materials, artificial flowers, dolls, internal laminates of rolls of dot printers for computers, sound-proofing materials, members requiring deformation restoration after impact absorption such as automobile bumpers and other parts, gap preventing materials of partitioning members for houses, portable vessels which are folded during non-use and restored in shape during use, mechanical devices such as coupling, etc., various heat shrinkable tubes, makeup material for human use, shape memory polymer foams, fibers, polymer composites, seal and gaskets, autochoke valves, sound insulation, and oil spill recovery.

Shape memory foams have a deformed shape and as-molded shape. They have their deformed shape when the polymer foam is compressed at a temperature higher than the $T_{trans}$ and kept compressed at a temperature lower than the $T_{trans}$ until the shape is set, and the as-molded shape is produced when the compressed polymer foam is heated again to a temperature higher than the shape recovery temperature until it recovers its original shape. Foams can be prepared by polymerizing materials in the presence of a foaming agent (i.e., a gas or low boiling solvent).

VII. Methods of Use

Certain articles of manufacture are intended to hold their intended shape unless acted upon in a manner inconsistent with their normal use. For example, a car bumper will hold its intended shape until it has been impacted. An article of manufacture that includes SMPs can be used in its intended shape, but if damaged (e.g. deformed) can be repaired, for example, by application of heat.

Other articles of manufacture are intended to be used such that the first shape is intended for an initial use, and a second shape is intended for a second use subsequent use. Examples of these articles include biomedical devices, which can form a second shape upon reaching body temperature or upon application of an external stimulus which heats the device above body temperature.

Other articles of manufacture are intended to be used such that the shape change that occurs in response to a temperature change triggers a particular action, such as activating a mechanical or electrical switch. For example, the switch could aid in regulating the temperature of the SMP environment, such as in temperature sensors and automatic chokes for automobiles.

The present invention will be further understood with reference to the following non-limiting examples.

EXAMPLE 1

Copolyesterurethane Shape Memory Polymers

A group of biocompatible and biodegradable multiblock-copolymers showing a thermal shape memory effect was synthesized. These polymers were composed of a crystallizable hard segment ($T_m$) and a soft segment having a thermal transition temperature $T_{trans}$ between room and body temperature. In contrast to the prior art segmented polyurethanes, the hard segment was an oligoester or an oligoetherester and did not contain any aromatic component.

Figure 6:
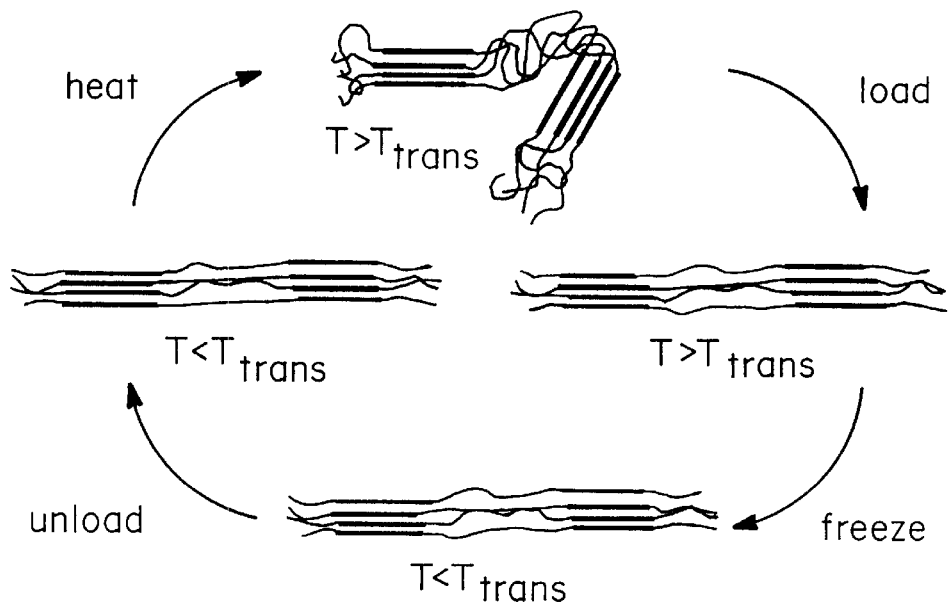
FIG. 6 is an illustration of the mechanism of the thermal shape memory effect for a multi-block copolymer.

The mechanism for programming the temporary shape and recovering the permanent shape of a multiblock-copolymer is shown in FIG. 6. The permanent shape of the materials was set by melting the polymer and cooling above $T_{trans}$ (FIG. 6—top pos.). Then, the polymer was formed into its temporary shape (FIG. 6—right pos.), which was fixed by cooling below $T_{trans}$ (FIG. 6—bottom pos.). After unloading, the permanent shape was recovered by reheating above $T_{trans}$. Synthesis of Telechelics, oligomers with functional groups at both ends.

The telechelic macrodiol were synthesized by ring opening polymerization of cyclic monomers with di(n-butyl) tinoxide as a transesterfication catalyst under a $N_2$ atmosphere.

Hard Segment

α,ω-dihydroxy [oligo(ethylene glycol glycolate) ethylene oligo (ethylene glycol glycolate)]-(PDS1200 and PDS1300) was prepared as follows. The monomer p-dioxane-2-one was obtained by distillation (thermal depolymerization) of the oligomer prior to use. 57 g (0.63 mol) of the monomer, 0.673 g (10.9 mmol) ethylene glycol, and 0.192 g (0.773 mmol) di(n-butyl) tinoxide were heated to 80° C. for 24 h. The end of the reaction (equilibrium) was determined by GPC. The product was soluted in hot 1,2-dichloroethane and filtered hot through a Buechner-funnel filled with silica gel. The product was obtained by precipitation in hexanes and dried in vacuo for 6 h.

Soft Segment i. Crystalline

Poly(ε-caprolactone)-diols with different $M_n$ are commercially available, for example, from Aldrich and Polysciences. PCL-2000 was used herein.

ii. Amorphous

α,ω-dihydroxy [oligo(L-lactate-co-glycolate) ethylene oligo (L-lactate-co-glycolate)]-(abbr.: PLGA2000-15) was prepared as follows. In a 1000 ml two-neck round bottomed flask, 300 g (2.08 mol) of L,L-dilactide, 45 g (0.34 mol) of diglycolide and 4.94 g (0.80 mol) ethylene glycol were heated to melt at 40° C. and stirred. 0.614 g (2.5 mmol) di(n-butyl) tinoxide was added. After 7 h, the reaction reached equilibrium as determined by GPC. The reaction mixture was soluted in 1,2-dichloroethane and purified in a silica gel column. The product was obtained by precipitation in hexanes and dried in vacuo for 6 h.

Properties of Telechelics

The molecular weight $M_n$ and thermal properties of the macrodiols were determined as shown in Table 1 below.

TABLE 1

Molecular Weight and Thermal Properties of the Macrodiols

| Label | $M_n$ GPC [g · mol$^{-1}$] | $M_n$ VPO [g · mol$^{-1}$] | $T_m$ [° C.] | ΔH [J · g$^{-1}$] | $T_g$ [° C.] | $\Delta C_p$ [J · g$^{-1}$] |
|---|---|---|---|---|---|---|
| PCL2000 | 1980 | 1690 | 43 | 73.5 | <−40 | — |
| PDS1300 | 1540 | 1340 | 97 | 74.5 | <−20 | — |

TABLE 1-continued

Molecular Weight and Thermal Properties of the Macrodiols

| Label | $M_n$ GPC [g·mol$^{-1}$] | $M_n$ VPO [g·mol$^{-1}$] | $T_m$ [°C.] | $\Delta H$ [J·g$^{-1}$] | $T_g$ [°C.] | $\Delta C_p$ [J·g$^{-1}$] |
|---|---|---|---|---|---|---|
| PDS1200 | 2880 | 1230 | 95 | 75.0 | <-20 | — |
| PLGA2000 | 2020 | 1960 | — | — | 29.0 | 0.62 |

Synthesis of Thermoplastic Elastomers (Multiblock Copolymer)

In a 100 ml two-neck round-bottomed flask connected to a soxleth extractor filled with molecular sieve 0.4 nm, two different macrodiols (one hard segment and one soft segment) as described in Table 2 below were soluted in 80 ml 1,2-dichloroethane. The mixture was refluxed to dry by azeotropic extraction of the solvent. Freshly distilled trimethylhexane-1,6-diisocyanate was added with a syringe, and the reaction mixture was heated to 80° C. for at least 10 days. At regular intervals, samples of the mixture were taken to determine the molecular weight of the polymer by GPC. At the end of the reaction, the product was obtained by precipitating the polymer in hexanes and purified by repeatedly dissolving in 1,2-dichloroethane and precipiting in hexanes.

Multiblock copolymers were prepared from the following two types of polymers.

(i) PDC polymers contain poly(ε-caprolactone). $T_{trans}$ for the soft segment is the melting point.

(ii) PDL polymers contain a α,ω-dihydroxy [oligo(L-lactate-co-glycolate) ethylene oligo (L-lactate-co-glycolate)]. $T_{trans}$ for the soft segment is the glass transition point.

TABLE 2

Synthesis of Multiblock Copolymers

| Polymer | 1. Diol | m [g] | n [mmol] | 2. Diol | m [g] | n [mmol] | TMDI [mmol] | time [d] |
|---|---|---|---|---|---|---|---|---|
| PDC22 | PDS1200 | 3,0245 | 2,653 | PCL2k | 6,0485 | 3,024 | 5,738 | 10 |
| PDL23 | PDS1200 | 2,2787 | 2,000 | PLGA2k | 6.1443 | 3,070 | 5,163 | 10 |
| PDC27 | PDS1300 | 2,5859 | 1,724 | PCL2k | 5,3611 | 2,681 | 4,368 | 14 |
| PDC40 | PDS1300 | 3,6502 | 2,433 | PCL2k | 3,9147 | 1,957 | 4,510 | 13 |
| PDC31 | PDS1300 | 3,2906 | 2,194 | PCL2k | 4,8619 | 2,431 | 4,500 | 16 |
| PDL30 | PDS1300 | 3,7115 | 2,474 | PLGA2k | 4,0205 | 2,011 | 4,480 | 16 |

Properties of the Thermoplastic Elastomers

The physical, mechanical, and degradation properties determined for the compositions are provided in Tables 3–9 below.

The hydrolytic degradation behavior of the new materials were tested in buffer solution pH 7 at 37° C. It was shown that the polymers are completely degradable and their degradation rate can be adjusted by the concentration of easily hydrolysable ester bonds. The values for loss of relative mass $m_r=m(t_0)/m(t)$ in % at 37° C., and. loss of relative molecular weight $M_r=M_w(t)/M_w(t_0)$ in % at 37° C.:

The toxicity of two different multiblock-copolymers was investigated using a chicken egg test. It was shown that blood vessels developed regularly and their condition was not influenced by the polymer samples.

TABLE 3

Composition of the Copolyester Urethanes Determined by 400 MHz $^1$H-NMR-Spectroscopy

| Label | Hard Segment | Weight Content [%]* | Soft Segment | Weight Content [%]* |
|---|---|---|---|---|
| PDL23 | PDS | 23.0 | PLGA | 54.2 |
| PDL30 | PDS | 30.0 | PLGA | 52.1 |
| PDC22 | PDS | 22.0 | PCL | 64.5 |
| PDC27 | PDS | 27.0 | PCL | 61.1 |
| PDC31 | PDS | 31.1 | PCL | 55.4 |
| PDC40 | PDS | 40.4 | PCL | 46.2 |

*The difference to 100% is the urethane content.

TABLE 4

Molecular Weight $M_w$ of the Copolyester Urethanes Films Determined by Multidetector-GPC

| | Polymer Film | | |
|---|---|---|---|
| Label | $M_w$ (LS) [g·mol$^{-1}$] | $M_w$ (Visc) [g·mol$^{-1}$] | dn/dc [ml·g$^{-1}$] |
| PDL23 | 161,500 | 149,000 | 0.065 |
| PDL30 | 79,100 | 83,600 | 0.057 |
| PDC22 | 119,900 | 78,500 | 0.078 |
| PDC27 | 72,700 | 61,100 | 0.080 |
| PDC31 | 110,600 | 108,600 | 0.065 |
| PDC40 | 93.200 | 86.300 | 0.084 |

TABLE 5

Transition Temperatures $T_m$ and $T_g$, Enthalpies of Fusion $\Delta H_m$ and Change in Heat Capacity $\Delta c_p$ of the Polymer Films from DSC Measurements (Values Given from Second Heating Process)

| Label | $T_{m1}$ [°C.] | $\Delta H_{m1}$ [J·g$^{-1}$] | $T_g$ [°C.] | $\Delta C_p$ [J·g$^{-1}$] | $T_{m2}$ [°C.] | $\Delta H_{m2}$ [J·g$^{-1}$] |
|---|---|---|---|---|---|---|
| PDL23 | — | — | 34.5 | 0.38 | — | — |
| PDL30 | — | — | 33.5 | 0.25 | 85.0 | 8.5 |
| PDC22 | 35.0 | 26.0 | — | — | — | — |
| PDC27 | 37.0 | 25.0 | — | — | 75.5 | 3.5 |
| PDC31 | 36.5 | 28.5 | — | — | 76.5 | 5.5 |
| PDC40 | 35.0 | 7.0 | — | — | 77.5 | 7.0 |

TABLE 6

Mechanical Properties of Polymer Films at 50° C. from Tensile Tests

| Code | E-Modulus [MPa] | $\epsilon_r$ [%] | $\sigma_r$ [MPa] | $\epsilon_{max}$ [%] | $\sigma_{max}$ [MPa] |
|---|---|---|---|---|---|
| PDC27 | 1.5 | 1,350 | 2.1 | 1,300 | 2.3 |
| PDC31 | 1.5 | 1,400 | 4.9 | 1,300 | 5.4 |
| PDC40 | 4.0 | 1,250 | 5.8 | 1,300 | 5.9 |
| PDL30 | 2.0 | 1,400 | 2.1 | 1,250 | 2.3 |

TABLE 7

PDL22 Degradability

| Degradation Time [d] | $M_r$ (viscosimetry) [%] | $M_r$ (light scattering) [%] |
|---|---|---|
| 14 | 81.3 | 85.7 |
| 21 | 67.1 | 74.6 |
| 29 | 62.9 | 65.6 |
| 42 | 43.6 | 47.7 |
| 56 | 54.4 | 41.9 |

TABLE 8

PDL23 Degradability

| Degradation Time [d] | $M_r$ (viscosimetry) [%] | $M_r$ (light scattering) [%] |
|---|---|---|
| 14 | 61.1 | 87.3 |
| 21 | 40.7 | 76.7 |
| 29 | 32.8 | 62.2 |
| 42 | 17.4 | 46.7 |
| 56 | 16.9 | 18.5 |

TABLE 9

Loss of Relative Mass

| Degradation Time [%] | PDC22 $m_r$ [%] | PDL23 $m_r$ [%] |
|---|---|---|
| 14 | 99.2 | 98.1 |
| 21 | 99.3 | 97.5 |
| 29 | 98.6 | 97.2 |
| 42 | 98.3 | 96.9 |
| 56 | 97.3 | 93.3 |

Shapes Memory Properties

Figure 7:
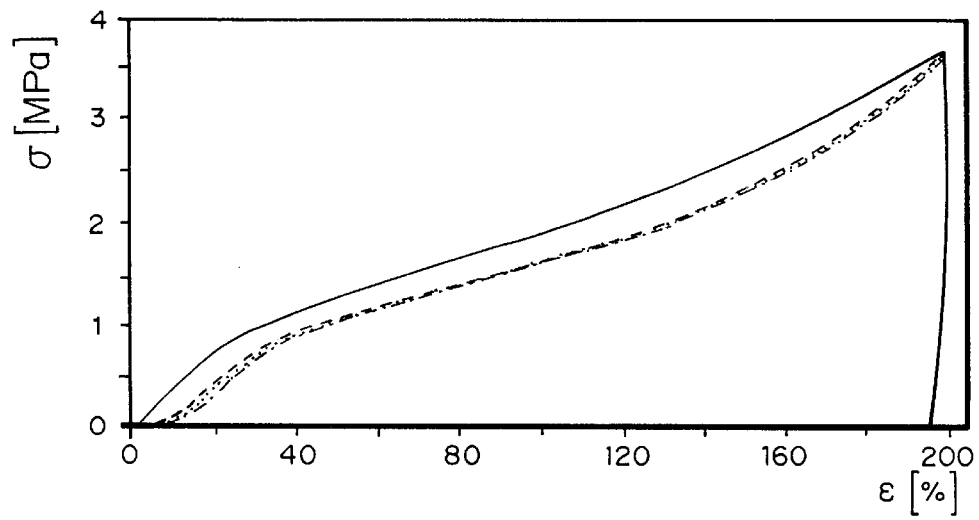
FIG. 7 is a graph showing stress versus elongation for a multi-block copolymer shape memory polymer.

FIG. 7 shows the results of tensile tests performed on the multiblock copolymers, as a function of the number of thermolytic cycles. The average shape fixity rate of thermocyclicly treated polymers and the dependency of strain recovery rates as a function of the number of cycles is shown below in Tables 10 and 11, respectively. The polymers have a high shape fixity, an equilibrium state was achieved after only two cycles.

TABLE 10

Average Shape Fixity Rate $R_f$

| Label | $R_f$ [%] |
|---|---|
| PDC27 | 97.9 |
| PDC40 | 96.2 |
| PDL30 | 97.7 |

TABLE 11

Cycle Number Dependence of Strain Recovery Rates $R_r$

| Number of Cycles | PDC27 $R_r$ [%] | PDC40 $R_r$ [%] | PDL23 $R_r$ [%] |
|---|---|---|---|
| 2 | 77.3 | 73.7 | 93.8 |
| 3 | 93.2 | 96.3 | 98.8 |
| 4 | 98.5 | 98.7 | 98.9 |
| 5 | 98.5 | 98.7 | 98.8 |

EXAMPLE 2

Degradable Shape Memory Thermoset With Crystallizable Soft Segment

A range of poly(ε-caprolactone) dimethacrylates and thermosets were evaluated for their mechanical and shape memory properties.

Synthesis of Macromonomer

Poly(ε-caprolactone) dimethacrylates (PCLDMAs) were prepared as follows. To a solution of poly(ε-caprolactone) diol with $M_n$=2,000 gmol$^{-1}$ (20.0 g, 10 mmol) and triethylamine (5.3 mL, 38 mmol) in 200 mL of dry THF, methacryloyl chloride (3.7 mL, 38 mmol) was added dropwise at 0°C. The solution was stirred at 0° C. for 3 days and precipitated salt filtered off. After concentrating the mixture at room temperature under reduced pressure, 200 mL of ethyl acetate was added, and the solution filtered again and precipitated into a ten-fold excess of a mixture of hexanes, ethyl ether, and methanol (18:1:1). The colorless precipitate was collected, soluted in 200 mL of dichloroethane, precipitated again, and dried carefully at room temperature at reduced pressure.

Synthesis of Thermosets

The macromonomer (or the monomer mixture) was heated to 10° C. above its melting temperature ($T_m$) and filled into a mould formed by two glass plates (25 mm×75 mm) and a teflon spacer of 0.60 mm thickness. To achieve a good homogenity, the mould was stored at $T_m$ for another hour. Photocuring was performed on a heated plate at $T_m$ for 15 min. The distance between heat lamp head and sample was 5.0 cm. After cooling to room temperature, the sample was extracted and swollen with a 100-fold excess of dichloromethane overnight and washed carefully. Finally, the sample was dried at room temperature under reduced pressure.

Properties of Macromonomers and Thermosets

Table 12 below lists the poly(ε-caprolactone) dimethacrylates that were prepared, along with the respective degree of acrylation ($D_a$) (%) The number following PCLDMA is the molecular weight M. of the poly(ε-caprolactone) diol used in the synthesis as determined using $^1$H-NMR and GPC, rounded to 500.

TABLE 12

Poly(ε-caprolactone) Diol and Degree of Acrylation

| Name | $D_a$ [%] |
|---|---|
| PCLDMA1500 | 87 |
| PCLDMA2000 | 92 |
| PCLDMA3500 | 96 |
| PCLDMA4500 | 87 |
| PCLDMA6500 | 93 |
| PCLDMA7000 | 85 |
| PCLDMA10000 | 86 |

Figure 8:
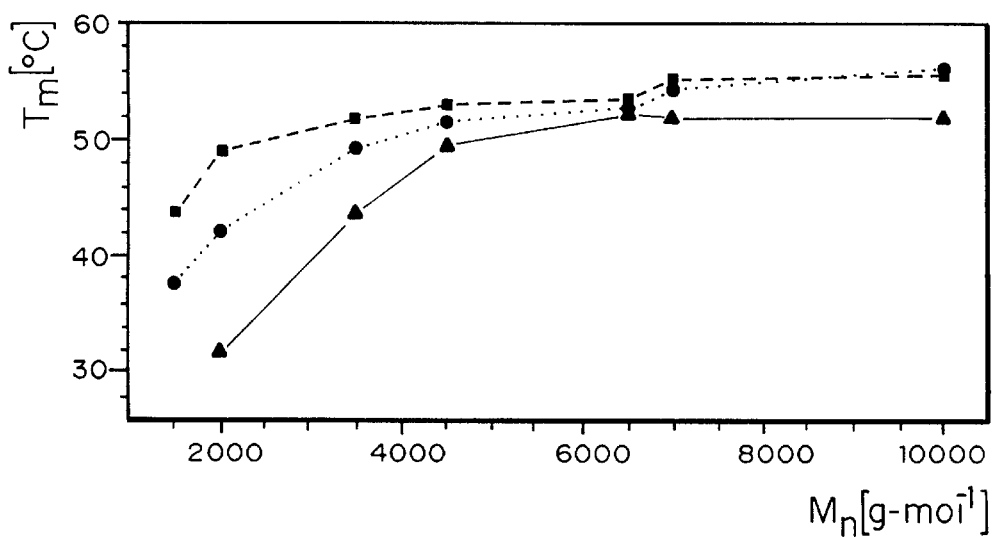
FIG. 8 is a graph showing the melting temperature of diols, dimethacrylates, and thermosets of poly($\epsilon$-caprolactone) as a function of the molar mass weight $M_n$ of the macromonomers.

FIG. 8 shows the melting temperature ($T_m$) of diols, dimethacrylates, and thermosets of poly(ε-caprolactone) as a function of the molar mass weight $M_n$ of the macromonomers. In the graph, macrodiols are represented by - -■- -; macromoners by . . . ● . . . ; and thermosets by —▲—.

The tensile properties of poly(ε-caprolactone) thermosets C1 through C7 at room temperature are shown below in Table 13, wherein E is the elastic modulus (Young's modulus), $\epsilon_s$ is the elongation and $\sigma_s$ is the stress at the yield point, $\sigma_{max}$ is the maximum stress, $\epsilon_{max}$ is the elongation at $\sigma_{max}$, $\epsilon_R$ is the elongation at break, and $\sigma_R$ is the stress at break. Table 14 provided below shows the tensile properties of the same poly(ε-caprolactone) thermosets at 70° C.

TABLE 13

Thermoset Tensile Properties at Room Temperature

| name | E [MPa] | $\epsilon_s$ [%] | $\sigma_s$ [MPa] | $\epsilon$max [%] | $\sigma$max [MPa] | $\epsilon$R [%] | $\sigma$R [MPa] |
|---|---|---|---|---|---|---|---|
| C1 | 2.4 ± 0.6 | — | — | 16.1 ± 2.0 | 0.4 ± 0.1 | 16.1 ± 2.3 | 0.38 ± 0.02 |
| C2 | 35 ± 3 | — | — | 20.6 ± 0.3 | 4.7 ± 0.1 | 20.6 ± 0.3 | 4.7 ± 0.1 |
| C3 | 38 ± 1 | 48 ± 1 | 11.2 ± 0.1 | 180 ± 20 | 12.1 ± 1.2 | 190 ± 20 | 11.7 ± 1.6 |
| C4 | 58 ± 4 | 54 ± 1 | 12.2 ± 0.1 | 247 ± 4 | 13.6 ± 1.9 | 248 ± 13 | 15.5 ± 2.7 |
| C5 | 72 ± 1 | 56 ± 2 | 15.5 ± 0.2 | 275 ± 10 | 15.6 ± 1.7 | 276 ± 6 | 15.0 ± 1.0 |
| C6 | 71 ± 3 | 43 ± 2 | 14.2 ± 0.1 | 296 ± 14 | 15.5 ± 0.2 | 305 ± 8 | 13.8 ± 2.7 |
| C7 | 71 ± 2 | 42 ± 5 | 13.6 ± 0.2 | 290 ± 30 | 16.2 ± 0.5 | 290 ± 30 | 15.7 ± 0.9 |

TABLE 14

Thermoset Tensile Properties at 70° C.

| name | E [MPa] | $\sigma_{max}$ [MPa] | $\epsilon$R [%] |
|---|---|---|---|
| C1 | 1.84 ± 0.03 | 0.40 ± 0.08 | 24 ± 6 |
| C2 | 2.20 ± 0.12 | 0.38 ± 0.05 | 18 ± 2 |
| C3 | 6.01 ± 0.12 | 2.05 ± 0.21 | 43 ± 9 |
| C4 | 2.30 ± 0.16 | 0.96 ± 0.01 | 61 ± 3 |
| C5 | 1.25 ± 0.08 | 0.97 ± 0.15 | 114 ± 13 |
| C6 | 1.91 ± 0.11 | 1.18 ± 0.06 | 105 ± 11 |
| C7 | 0.70 ± 0.09 | 0.79 ± 0.10 | 210 ± 7 |

Shape Memory Properties

The thermosets were determined to have the thermomechanical properties indicated in Table 15. The number average molecular weights ($M_n$) is of the macromonomer. The lower limit temperature, $T_l$, is 0° C., and the higher limit temperature, $T_h$, is 70° C. The extension in the temporary shape is 50%. $R_r(2)$ is the strain recovery rate of the second cycle, $R_{r,tot}$ is the total strain recovery rate after 5 cycles, $R_f$ is the average strain fixity rate.

TABLE 15

Thermoset Thermomechanical Properties

| name | $M_n$ [g · mol$^{-1}$] | $R_r$ (2) [%] | $R_{r,tot}$ [%] | $R_f$ [%] |
|---|---|---|---|---|
| C4 | 4,500 | 93.3 | 93.0 | 93.9 ± 0.2 |
| C5 | 6,500 | 96.3 | 94.5 | 93.9 ± 0.2 |
| C6 | 7,000 | 93.8 | 92.1 | 92.5 ± 0.1 |
| C7 | 10,000 | 98.6 | 96.8 | 86.3 ± 0.5 |

Modifications and variations of the polymeric compositions and methods of preparation and use thereof will be obvious to those skilled in the art from the foregoing detailed description. Such modifications and variations are intended to come within the scope of the appended claims.

We claim:

1. A shape memory polymer composition having at least two shapes in memory.

2. The composition of claim 1 comprising:
   a) at least one hard segment which has a $T_{trans}$ between −40 and 270° C.,
   b) a first soft segment which has a $T_{trans}$ at least 10° C. lower than that of the hard segment(s), which is linked to at least one hard segment,
   c) a second soft segment, linked to at least one of the hard segment or first soft segment, which has a $T_{trans}$ at least 10° C. less than the $T_{trans}$ of the first soft segment.

3. The composition of claim 2 wherein the $T_{trans}$ of the hard segment is in the range of between 30 and 150° C.

4. The composition of claim 3 wherein the $T_{trans}$ of the hard segment is in the range of between 30 and 100° C.

5. The composition of claim 2 wherein the $T_{trans}$ of the first soft segment(s) is at least 20° C. below that of the hard segment(s).

6. The composition of claim 2 wherein the $T_{trans}$ of the second soft segment(s) is at least 20° C. below that of the first soft segment(s).

7. The composition of claim 1 wherein the shape memory polymer comprises a thermoplastic polymer.

8. The composition of claim 1 wherein the polymer comprises multiple segments, and the molecular weight $M_n$ of at least one of the segments is between about 500 and 10,000.

9. The composition of claim 1 wherein the shape memory polymer is selected from the group consisting of graft polymers, linear polymers, and dendrimer polymers.

10. The composition of claim 1 wherein the polymer comprises hard and soft segments and the hard segment comprises cyclic moieties.

11. The composition of claim 10 wherein the moieties are selected from the group consisting of crown ethers and cyclic oligopeptides.

12. The composition of claim 1 wherein the shape memory polymer is biodegradable.

13. The composition of claim 12 wherein the polymer comprises hard and soft segments and at least one of the hard and soft segments is selected from the group consisting of polyhydroxy acids, polyorthoesters, polyether esters, polyesters, polyamides, polyesteramides, polydepsidpetides, aliphatic polymrethanes, polysaccharides, polyhydroxyalkanoates, and copolymers thereof.

14. The composition of claim 13 wherein the polyether ester is selected from the group consisting of oligo (p-dioxanone) and its copolymers.

15. The composition of claim 1 wherein the polymer comprises at least two soft segments and the segments are connected via a linkage that is cleavable by application of a stimuli selected from the group consisting of ultrasound, electric field, magnetic field, and light.

16. The composition of claim 1 wherein the polymer comprises at least one hard segment and at least one soft segments, wherein the ratio by weight of the hard segment-:soft segment is between about 5:95 and 95:5.

17. The composition of claim 1 comprising
a thermoset polymer that comprises at least two covalently crosslinked soft segments, wherein
a first soft segment has a $T_{trans}$ between 250° C. and 40° C.; and
a second soft segment linked to the first soft segment has a $T_{trans}$ at least 10° C. less than the $T_{trans}$ of the first soft segment.

18. The composition of claim 17 wherein the first soft segment has a $T_{trans}$ between 200° C. and 0° C.

19. The composition of claim 17, wherein at least one of the soft segiments contains a crosslinkable group, and wherein at least one of the soft segments are linked by formation of an interpenetrating network or a semi-intepenetrating network.

20. The composition of claim 17 wherein the soft segments form a mixed interpenetrating network.

21. The composition of claim 17 wherein the soft segments form a shape memory semi-IPN consisting of a thermoset polymer having at least one soft segment and a homo- or copolymer.

22. The composition of claim 21 wherein the resulting semi-IPN has a highest $T_{trans}$ in the range of 200 and -40C.

23. The composition of claim 21 wherein the thermoset polymer is degradable.

24. The composition of claim 21 wherein the homo- or copolymer or thermoset copolymer is degradable.

25. The composition of claim 21 having a multi shape memory where the number of shapes in memory is the same as the number of thermal transitions of the polymer.

26. The composition of claim 1 comprising a shape memory IPN comprising an interpenetrating network of thermoset polymers.

27. The composition of claim 1 comprising a shape memory mixed-IPN comprising a thermoplastic elastomer containing at least one hard segment and at least one soft segment and a thermoset containing at least one soft segment.

28. A shape memory polymer composition comprising:
a) at least one hard segment which has a $T_{trans}$ between -30 and 270° C.,
b) at least one soft segment which has a $T_{trans}$ at least 10° C. lower than that of the hard segment(s), which is linked to at least one hard segment,
wherein at least one of the hard or soft segments includes a functional group which is able to form a crosslink that can be cleaved under application of a stimuli selected from the group consisting of light, electric field, magnetic field, and ultrasound.

29. A shape memory polymer composition comprising hard and soft segments wherein at least one of the hard and soft segments undergoing solid to solid state transitions wherein the polymer has two or more shapes in memory.

30. A shape memory polymer composition wherein the polymer has a physical crosslink on the basis of ionic interactions involving polyelectrolyte segments or supramolecular effects based on highly organized hydrogen bonds and wherein the polymer has two or more shapes in memory.

31. A method for forming a shape memory article with two or more shapes in memory comprising:
a) preparing a shape memory polymer composition comprising:
i) at least one hard segment which has a $T_{trans}$ between -30 and 270° C.,
ii) a first soft segment which has a $T_{trans}$ at least 10° C. lower than that of the hard segment(s), which is linked to at least one hard segment,
iii) a second soft segment, linked to at least one of the hard segment and first soft segment, which has a $T_{trans}$ at least 10° C. less than the $T_{trans}$ of the first soft segment;
b) heating the composition above the $T_{trans}$ of the hard segment;
c) shaping the composition to form a desired first shape;
d) cooling the composition to a temperature below the $T_{trans}$ of the hard segment and above the $T_{trans}$ of the first soft segment to harden the hard segment while keeping the first and second soft segments in a melted or amorphous state;
e) shaping the composition to form a desired second shape;
f) cooling the composition below $T_{trans}$ of the first soft segment and above the $T_{trans}$ of the second soft segment to fix the second shape;
g) shaping the composition to form a desired third shape; and
h) cooling the composition below the $T_{trans}$ of the second soft segment to fix the third shape.

32. The method of claim 31 wherein the composition is shaped by extrusion or injection molding.

33. The method of claim 32 further comprising heating the composition above the $T_{trans}$ of the second soft segment to return the composition to the second shape.

34. The method of claim 33 further comprising heating the composition above the $T_{trans}$ of the first soft segment to return the composition to the first shape.

35. The method of claim 34 further comprising heating the composition above the $T_{trans}$ of the hard segment, thereby causing the composition to lose the memory of the first and second shapes.

36. A method of forming a composition with a shape in memory comprising:
a) preparing a polymeric composition comprising:
i) at least one hard segment which has a $T_{trans}$ between -30 and 270° C.,
ii) at least one soft segment which has a $T_{trans}$ at least 10° C. lower than that of the hard segment(s), which is linked to at least one hard segment,
wherein at least one of the hard or soft segments includes a functional group which is able to form a crosslink that can be cleaved under application of a stimuli selected from the group consisting of light, electric field, magnetic field, and ultrasound;

b) heating the composition above the $T_{trans}$ of the hard segment;

c) shaping the composition to form a desired first shape;

d) cooling the composition to a temperature below the $T_{trans}$ of the hard segment and above the $T_{trans}$ of the soft segment;

e) shaping the composition to form a desired second shape; and f) fixing the second shape by forming cleavable crosslinks.

37. The method of claim 36 further comprising g) forming the composition into a third shape and cooling below $T_{trans}$ of the soft segment.

38. The method of claim 37 further comprising returning the composition into the second shape by heating above $T_{trans}$ of soft segment but lower than $T_{trans}$ of hard segment.

39. The method of claim 38 further comprising returning the composition into the first shape by application of a stimulus selected from the group consisting of light, electric field, magnetic field, and ultrasound.

40. The composition of any of claims 1, 28 or 29 comprising polymer blends.

41. The composition of claim 30, wherein a polycationic metal salt links at least two segments, wherein the link formed can be cleaved using an aqueous solvent.

42. The composition of claim 1 wherein the shape memory polymer comprises a covalently crosslinked polymer.

43. The composition of claim 1 further comprising a shape memory thermoset polymer which comprises at least one covalently crosslinked soft segment, the covalently crosslinked soft segment having a $T_{trans}$ between −30 C and 270 C and comprising a functional group which is able to form a second crosslink which can be cleaved by application of a stimuli selected from the group consisting of ultrasound, electric field, magnetic field, and light.

44. The composition of claim 27 wherein the thermnoplgstic elastomer is degradable.

* * * * *